United States Patent [19]

Scott

[11] 4,170,144
[45] Oct. 9, 1979

[54] MATERIAL SCANNING APPARATUS
[75] Inventor: William R. Scott, Doylestown, Pa.
[73] Assignee: The United States of America as represented by the Secretary of the Navy, Washington, D.C.
[21] Appl. No.: 846,231
[22] Filed: Oct. 27, 1977
[51] Int. Cl.$^2$ .......................................... G01N 29/00
[52] U.S. Cl. ....................................................... 73/609
[58] Field of Search ................. 73/579, 582, 602, 616, 73/618, 620, 624, 627, 630, 609, 610

[56] References Cited
U.S. PATENT DOCUMENTS

| | | | |
|---|---|---|---|
| 2,989,864 | 6/1961 | Bamford | 73/620 |
| 3,043,132 | 7/1962 | Schubring | 73/579 |
| 3,220,248 | 11/1965 | Wood | 73/616 |
| 3,276,249 | 10/1966 | King | 73/630 |
| 3,474,664 | 10/1969 | Mitchel et al. | 73/616 |
| 3,538,751 | 11/1970 | Gericke | 73/616 |
| 3,623,358 | 11/1971 | Sugimoto | 73/579 |
| 4,008,602 | 2/1977 | Love | 73/609 |
| 4,063,450 | 12/1977 | Lyons | 72/579 |

*Primary Examiner*—Daniel M. Yasich
*Attorney, Agent, or Firm*—R. S. Sciascia; Henry Hansen; Stanton D. Weinstein

[57] ABSTRACT

Apparatus and method for producing maps of thickness or elastic constant variations of nominally plane sheet or plate materials. Amplitude variation at a set frequency on a normal resonance peak is recorded to determine resonance peak variation and thus specimen thickness or elastic constant variation. A mechanical scanner moves a transducer across the material submerged in a water tank for performing an ultrasonic C-scan. A transmitter or pulse generator repeatedly pulses the transducer to produce a focused narrow pulse of ultrasound which reverberates within the material. Echoes from the material in response to the pulse are received by the same or another synchronously moving transducer, whose resulting signal then passes through a gate, which removes extraneous signals and selects the number of multiple echoes and thus amplitude range desired, and a variable filter controlled by a function generator which selects the desired frequency, to a pen recorder. The desired frequency is selected at or near a resonance peak for the material. The variable filter produces a signal in the desired narrow frequency band whose amplitude variation is indicative of variation in the material's properties with position of the transducer. The amplitude of the gated filtered signal is used to control the intensity of the recorder, which moves synchronous with the motion of the transducer. The recorder produces a map of the material at the desired frequency.

10 Claims, 4 Drawing Figures

MATERIAL SCANNING APPARATUS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to non-destructive measuring and testing systems, and more particularly to systems for scanning and mapping properties of materials.

One prior practice has been to measure thickness of a specimen of material by passing a pulse of ultrasound therethrough and measuring the time interval between reception of response echoes from the front and back surfaces of specimen. Because of the presence of interfering noise and other signals, the first and second peaks of the specimen reflected response signal are detected to determine the appropriate specimen echo response time. Peak detection depends upon the amplitude or the shape of the detected response signal, both of which can vary substantially for such response signals, making peak detection difficult and unreliable. Furthermore, since the material response generally consists of multiple echoes in the time domain, the peaks from these multiple echoes can overlap, particularly for a sufficiently thin specimen, making detection and distinction of individual peaks difficult, thereby making accurate determination of material response time difficult. Moreover, where the two peaks would overlap or nearly overlap, the two signals would interfere and displace their peaks towards each other, introducing inaccuracies into thickness measurement. Also, the relative amplitude of the second peak with respect to the first peak varies greatly from material to material, so that second peak detection is made that much more difficult.

SUMMARY OF THE INVENTION

Accordingly, it is the general purpose of the invention to provide material scanning apparatus capable of non-destructively mapping minute variations in parameters of materials.

Other objects of the present invention are to provide material scanning apparatus capable of making a large number of measurements at different locations on a material specimen with high accuracy, in reflection, transmission or reflector plate modes, locating defects in materials with high accuracy, predicting the precise location of material failure, measuring the general quality of the material, mapping minute variations in thickness, elastic constant or speed of sound for materials, and providing a visual display of variation of material properties with location or position in the material.

Further objects of the present invention are to provide material scanning apparatus whose accuracy is unaffected by overlapping multiple response echoes from the material being studied, by thin specimens, by ranges in response signal amplitude or shape, nor by echo amplitude variation from material to material, and which is simple, inexpensive, reliable, easily kept in alignment, has a rapid response and is capable of making rapid measurements.

Briefly, these and other objects of the present invention are accomplished by material scanning apparatus wherein the material specimen under study is scanned and interrogated via a transducer with a repeated pulse of energy such as ultrasound. The response of the specimen is received by the same or another synchronously moving transducer and provided therefrom to a time-gate which eliminates unwanted signals by permitting the response signal to pass therethrough only at a preset time after production of the interrogation pulse and for a preset duration, thereby only permitting a portion of the response pulse to pass therethrough. The gated response signal is then received by and filtered by a variable filter which is controlled by a function generator to only permit a very narrow frequency band of the gated response signal to pass therethrough. The function generator selects a frequency on a resonance peak of the frequency-domain spectrum of the material. The frequency position of the peak shifts in the spectrum with changes in the specimen response to the interrogation pulses. Such changes result from changes in material properties with changes in position of interrogation during a scan. The filtered gated response signal then passes through a rectifier and a low-pass filter to produce a slowly varying direct current signal whose amplitude is proportional to a material property of the specimen. This amplitude is used to control the intensity or darkness of a recorder at a point whose planar coordinates are controlled by and correspond to those of the scanner and transducer interrogating the material specimen.

Other objects, advantages and novel features of the invention will become apparent from the following detailed description of the invention when considered in conjunction with the accompanying drawings wherein:

DESCRIPTION OF THE PREFERRED EMBODIMENT

The response of material specimens to ultrasonic interrogation has a frequency spectrum consisting of a series of resonance peaks or extrema whose frequency location on the spectrum shift with variation in material properties such as thickness, modulus and speed of sound therein. Each such resonance peak or extrema is a highly localized peak or valley of high amplitude. Thus, if the nominal peak frequency of one of these peaks, or a frequency found in the leading or trailing edge of one of these peaks, such as a half-power point or the point of greatest slope, is constantly monitored during scanning and ultrasonic interrogation of the specimen S, the amplitude at that point will vary with variation in material properties with scanning position, as the abscissa of the resonance peak shifts therewith. Using the amplitude of such a fixed frequency to modulate the intensity of pen 34 of recorder 35 during scanning produces a map of the material having dark and light areas whose darkness or lightness indicates the magnitude of material properties at the corresponding location on the specimen. Thus, the variation in such properties with position on the specimen S is pictorially displayed.

Figure 1:
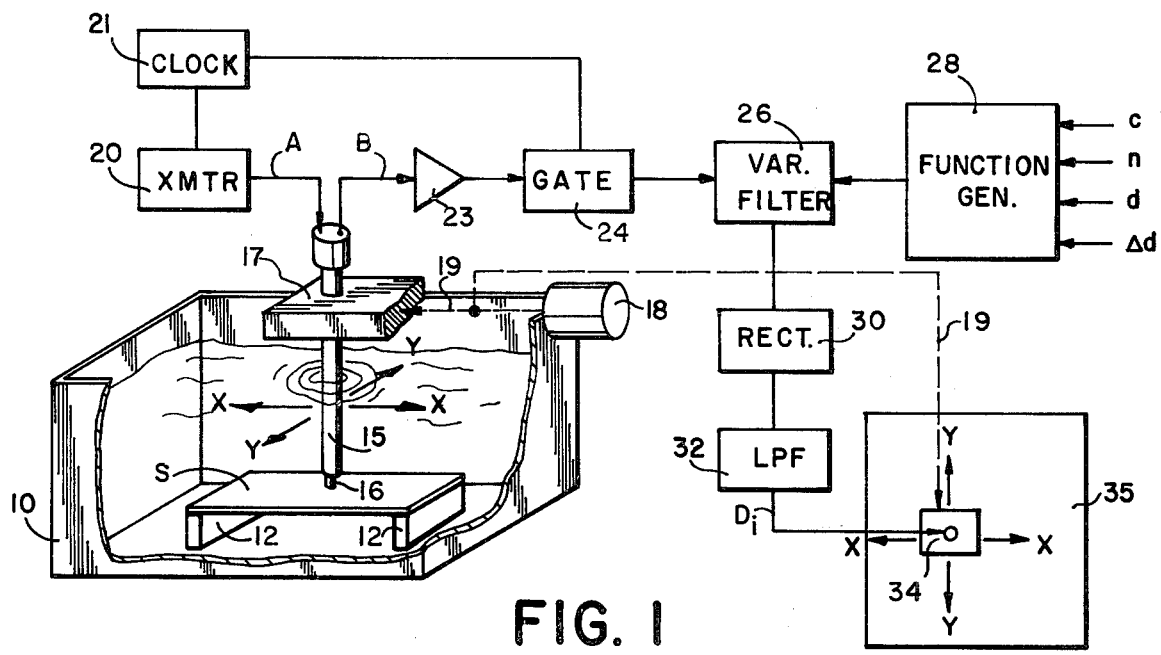
FIG. 1 is a diagrammatic representation of material scanning apparatus according to the present invention.
Figure 2:
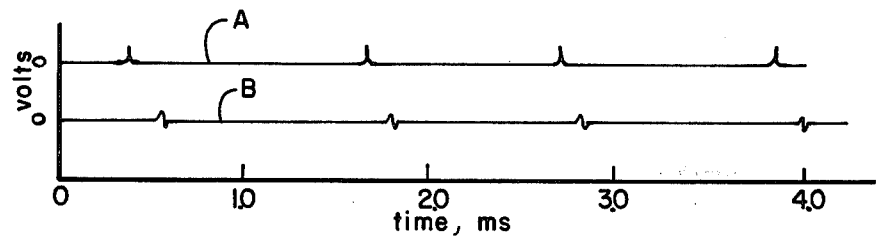
FIG. 2 is a waveform timing chart describing typical signals generated by and received by the apparatus of FIG. 1.

Referring now to the drawings, there is shown in FIG. 1 a material scanning apparatus, in particular an ultrasonic mapping system, for mapping of material properties of a material specimen S. Mapping of material properties of specimen S is accomplished by scanning the specimen with pulses of ultrasound produced by ultrasonic broad-band transducer 16 which also receives the localized response of the specimen to the pulses. For improved transmission of ultrasound between transducer 16 and specimen S, both specimen and transducer can be submerged in a liquid medium such as water in a tank 10, and transducer 16 can be placed a short distance, for example one inch, away from the surface of the specimen being scanned. To prevent interfering echoes from the bottom of tank 10 or from the support structure for specimen S, the specimen can be supported at two of its edges by supports 12, although such support at its corners with posts would also be suitable. Such interfering or unwanted or undesired signals can also be avoided by appropriate use of clock 21 and gate 24, as discussed hereinbelow. Transducer 16 is mounted on transducer mount 15 which is attached to and displaced by scanner 17. Conventional devices which can be utilized as transducer 16 or scanner 17 are well known in the art. Scanner 17 powered by motor means 18 via mechanical linkage 19 displaces transducer mount 15 and with it transducer 16 in the X and Y directions parallel to the surface being scanned of specimen S, in order to accomplish scanning of specimen S with pulses of ultrasound from transducer 16. For example, transducer 16 could be initially positioned at or near one corner of specimen S, with scanner 17 sweeping transducer 16 successively across the surface of the specimen in a direction parallel to one edge of the specimen, which sweeps are displaced from each other by very small distance steps or short displacements. This can be accomplished where motor means 18 comprises an oscillating or reversing motor for the sweeps and a stepping motor for advancing transducer 16 in short steps between sweeps in a direction perpendicular to the sweeps and parallel to the surface of specimen S. The sweeps can be parallel to each other and in the Y-direction shown in FIG. 1, and the inter-sweep steps can then be in the X-direction shown in FIG. 1. The duration of each sweep can for example be one second, and the duration of a complete scan of specimen S can for example be 20 minutes, for an 8 inch by 10 inch specimen, although longer or shorter times or durations can be employed depending on the accuracy desired. Pen 34 of plotter or recorder 35 is connected to mechanical linkage 19 to move on recorder 35 synchronously with movement of transducer 16 with respect to specimen S, so that each position of pen 34 on recorder 35 corresponds to a position of transducer 16 with respect to specimen S. Transducer 16 can for example be a focusing transducer producing a focused narrow beam or pulse of ultrasound. As transducer 16 moves with respect to specimen S, transmitter 20 produces at regular intervals, such as one millisecond, a pulse, as shown as signal A of FIG. 2, which signal comprises a series of pulses each of regular duration such as 0.02 to 1.0 microsecond and at regular intervals such as one millisecond. The timing of the pulses of signal A is determined by clock 21 connected to transmitter 20. Transmitter 20 and clock 21 can for example together be an Ultrasonic Pulser/Receiver Model 5050 PR described in Ultrasonic Technical Data Bulletin UTD-11 (Dec., 1973) copyright 1971 by Panametrics, Inc., Waltham, Massachusetts, and in *Instruction Manual: Ultrasonic Pulser-Receiver Model* 5050 PR by Panametrics, Inc. Clock 21 can, as another example, alternatively be a counter or shift register; see Morris, R. L. and Miller, J. R. eds. *Designing with TTL Integrated Circuits.* (N.Y., McGraw-Hill, 1971). Signal A is provided by transmitter 20 to transducer 16, causing transducer 16 to produce similarly regular pulses of ultrasound of similar duration and interval. This pulse of ultrasound is received by, reverberated within and reflected by specimen S, the reverberations producing a series of response signals of decreasing amplitude. The response signals are received by transducer 16 which converts them into electrical signals shown as signal B of FIGS. 2 and 3. The electrical signals are provided to and received by amplifier 23 approximately 50 microseconds after transmission by transmitter 20 of the corresponding pulse of signal A for which this is the response. Transducer 16 can for example be a piezoelectric transducer capable of producing an acoustic or ultrasonic signal with electric excitation and producing an electric signal upon sensing acoustic excitation such as the returning wave B. Transducer 16 upon receiving a signal A pulse from transmitter 20 produces a focused narrow pulse of ultrasound for interrogation of specimen or sample S. This pulse reverberates within specimen S and causes a material response in the form of a series of multiple echoes which are received by the transducer 16. Transducer 16 converts these echoes to an electrical signal B which is provided to amplifier 23. Amplifier 23 amplifies response signal B and provides the amplified signal to timing gate 24 which removes extraneous signals such as signal A and reflection from the bottom of tank 10, and selects a time-base portion of duration tg of response signal B containing a number of multiple echoes. Timing gate 24 can for example be a Stepless Gate Model 5052G described in Bulletin UTD-12A (September 1973) and in *Instruction Manual: Stepless Gate Model 5052G*, both by Panametrics, Inc., Waltham, Massachusetts. The duration tg of gate 24 can, for example, be 10 microseconds. Clock 21 is connected to gate 24 to provide timing to gate 24 to prevent passage therethrough of extraneous signals, such as signal A at the beginning of a response signal, and the signal resulting from reflection from the bottom of tank 10 at the end of a response sequence of signals. Also, gate 24 can be configured to trigger upon reception of the first peak of a sequence of response signals in response to a signal A pulse, and can have a preset duration tg such as could be provided by a one-shot multivibrator having a preset duration which would remove the first peak of a sequence of response signals, select the desired time-portion of the response sequence or desired number of multiple echoes for a sufficiently sharp resonance peak, and remove extraneous signals following the sequence of response signals. Gate 24 should admit and permit to pass therethrough as much of, or remove as little of, the amplified sequence of response signals to enable sharper resonance peaks. The multiple echoes of signal B include first, the echo from the first interface, followed by the echo from the back interface and the first, second, third, etc. multiples. There can be 25 or more echoes in response to a single interrogation pulse, although later echoes can have such low amplitudes as to be undetectable over the ambient noise level. The echo from the first interface can be removed by gate 24 if desired because if gate 24 triggers on this part of the response sequence, it is difficult to retain it in the gated signal. Also, this portion of signal B is inverted with respect to the other echoes, a situation found only with reflected signals and not in the transmission or reflector plate modes. Accordingly, removal of the first echo would result in the same kind of spectra for all three modes of operation, although such removal is not absolutely necessary for proper operation. The gated signal produced by gate 24 is provided to variable filter 26 which is controlled by function generator 28 to produce a filtered signal having a very narrow bandwidth centered about a selected frequency determined by function generator 28 as discussed hereinbelow. Variable filter 26 can for example be a Hewlett-Packard Spectrum Analyzer RF Section 8553B and IF Section 8552B respectively described in Manual Part No. 08553-90039, *Operating and Service Manual: Spectrum Analyzer RF Section 8553B*, printed July 1971, and Manual Part No. 08552-90055, *Operating and Service Manual: Spectrum Analyzer IF Section 8552B*, printed Dec. 1972; copyright 1970 and 1971, respectively, by Hewlett-Packard Company, Palo Alto, California. Function generator 28 sets the central operating frequency produced by variable filter 26 at $f\text{operating} = cn/2d - cn\Delta d/2d^2$ where c is the speed of sound in the specimen, n is any integer, d is the nominal thickness of the specimen measured by any suitable means at least one point on the specimen and $\Delta d$ is the expected variation in specimen thickness. These four values can be provided to function generator 28 as preset values controlled by the operator such as via knobs. Obviously, it would appear to be well-known in the art to construct such a function generator, for example using an appropriate combination of multipliers, dividers, squarers, and subtractors (or inverters and adders), for the given function. See for example Kohavi, Z. *Switching and Finite Automata Theory*. (N.Y., McGraw-Hill, 1970), and *Signetics Data Manual* (Copyright 1976 by Signetics Corp., Sunnyvale, California). Obviously, an analog computer, or a digital computer or microprocessor in combination with a digital-to-analog converter, could also be utilized. Function generator 28 employing this function sets the central operating frequency on the leading edge of a resonance peak and spaced from the extremum of the peak by the expected frequency variation $\Delta f$. Thus, shift in resonance peak frequency in a single direction would not cause both darkening and then lightening, or vice versa, of the resulting map, which would confuse the user. Integer n corresponds to the order of the resonance peaks or extrema, and for a laminar specimen S should be less than the number of laminae. For mapping using the trailing edge of the peak, the minus sign in the above formula should be changed to a plus sign. The signal produced by variable filter 26 is demodulated to remove the carrier wave by being provided to rectifier 30 which can be a half-wave or a full-wave rectifier, whose signal is then passed through low pass filter 32, which can, for example, be set to filter out signals having frequencies of greater than 100 Hz to produce a slowly varying direct current signal $D_i$ whose amplitude modulates the intensity of pen 34 of recorder 35, so that the darkness or lightness of a point plotted by pen 34 is determined by the reverberation response to specimen S at the corresponding point on the specimen. The signal provided to pen 34 can be amplified by an amplifier if desired or needed for proper pen operation. The bandwidth of filter 26 can for example be one KHz. Two such signals $D_1$ and $D_2$, each from a different sweep of specimen S, are shown in FIG. 4, where it is clear that the portion of the specimen scanned during the $D_2$ sweep is thinner or thicker than the portion of the specimen scanned during the sweep for signal $D_1$, depending upon which edge of the resonance peak is used.

Alternatively, a pulser/receiver providing signal A to transducer 16 and receiving signal B therefrom can be substituted for transmitter 20 and amplifier 23. The pulser/receiver would also amplify the received response signal and provide it to gate 24. An oscilloscope can be used to set the timing and duration of gate 24 by pulsing specimen S before actually beginning the scan, and viewing sample response pulses, such as for noting where the sequence of response echoes trails off. A spectrum analyzer capable of converting a received signal to the frequency domain by performing a Fourier transform thereon and displaying the resulting frequency spectrum thereof, and capable of producing a portion of that signal centered about a desired frequency, can be used in lieu of variable filter 26 and function generator 28. If a spectrum analyzer is used, the frequency spectrum of the received amplified gated response signal would be inspected for resonance peaks, and an appropriate point on a resonance peak would be selected as the desired center bandpass frequency for the signal to be provided to pen 34.

Figure 3:
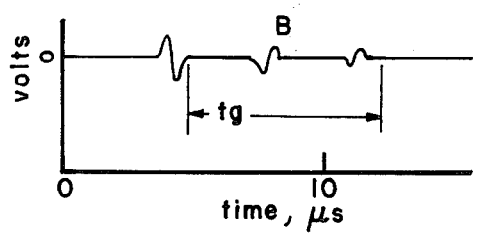
FIG. 3 is another waveform timing chart describing typical signals received by the apparatus of FIG. 1.
Figure 4:
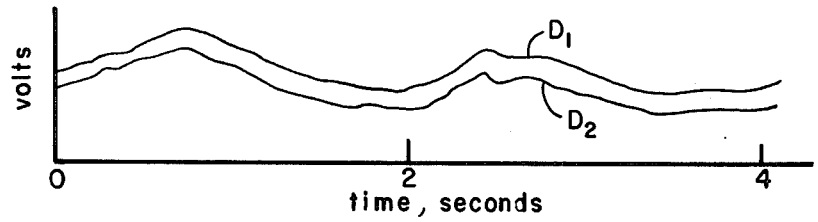
FIG. 4 is another waveform timing chart describing typical signals generated by the apparatus of FIG. 1.

As many as 20 or 25 or more echoes can result from interrogation of the material with a single ultrasonic pulse, although only three are shown in FIG. 3 for purposes of illustration.

The present invention can be operated in reflection, transmission or reflector-plate modes. In reflection mode, the interrogation signal is transmitted from and the response signal is received on the same side of the specimen S, as shown in FIG. 1. In the transmission mode, the interrogation pulse is transmitted from one side of the specimen S and received on the other side, requiring transducers on both sides of the specimen. Two transducers, one for transmission and one for reception, can also be used in the reflection mode. In the reflector-plate mode the interrogation signal is provided at one side of the specimen S, passes through the specimen, is reflected from a thick plate located beneath the specimen, and is passed through the specimen again to produce a transmission-type response with the interrogation and response signals appearing on the same side of the specimen, and with the interrogation and response equipment therefore both being located on the same side of the specimen.

The frequency domain spectrum of the gated amplified response signal consists of a series of resonance peaks spaced at frequencies which are integer n multiples of $c/2d$, where p is the density, d is the thickness of the specimen S and c is the speed of sound in the specimen which is given by $c = \sqrt{c_{33}/p}$ where $c_{33}$ is the elastic constant of the material referred to a direction normal to the surface of the specimen. For a response obtained by reflection, the spectrum consists of a series of deep spike-like valleys for the resonances whose nadirs are at the peak resonance frequencies. For transmission spectra, these valleys are inverted, so that the resonances take the form of peaks whose apexes correspond to the peak resonance frequency. A frequency-domain spectrum similar to that obtained for transmission responses is obtained in the reflector plate mode. This distinction between transmission and reflection spectra is removed if the first response echo or reverberation in the reflection mode is gated out, since this echo is inverted with respect to all succeeding echoes, a feature which does not appear in the transmission or reflector plate modes.

Recorder 35 produces a map wherein gray level corresponds to thickness. Small shifts in the resonance peak produce large changes in recorded gray level. Areas of increased thickness can be mapped either darker or lighter depending on which side of the resonance the operating frequency is selected. On the low-frequency side of a resonance peak, where the peak resonance frequency is located at the apex of the curve used, darkness is proportional to thickness, so that thin areas appear on the map as light areas and thick areas on the specimen appear as dark areas on the map. Conversely, where the operating frequency is selected on the high-frequency side of the resonance curve used, mapped darkness shown by recorder 35 is inversely proportional to specimen S thickness, so that thin specimen areas are shown as dark areas on the map and thick specimen areas are shown as light areas on the map produced by recorder 35. The converse is true where the resonance frequencies appear as minima or nadirs of valleys. For a gray level map it is preferred that the selected operating frequency not fall on both sides of a resonance peak, since darkness and lightness of the resulting map would not depend directly upon the increase or decrease in thickness or elastic constant, depending upon which property is being monitored and mapped, but upon absolute value variation of that property from a central value. Accordingly, function generator 28 keeps the frequency separation between the peak of the selected resonance curve and the selected operating frequency being monitored. This frequency separation is set at at least the value of the frequency shift expected from variation in the material property being monitored and mapped. If the high-frequency side of the selected resonance curve is used, the minus sign in the above formula should be changed to a plus sign.

Alternatively, a different type of thickness map can be made. Deviations from a given thickness can be recorded by selecting the operating frequency at a transmission peak, or reflection minimum or peak, of a resonance and operating recorder 35 near a cut-off threshold. A variation in the thickness of the specimen S will produce a shift in the resonance peak and a rapid intensity change. For any mode of operation, the peak resonance should be selected. Obviously, the differentiation between transmission and reflection modes is removed if the first response echo is gated out of the response signal B.

The same apparatus can be used to map variations in elastic constant or speed of sound for specimens, except that a different function generator 28 is used. The elastic constant for the specimen S is the partial differential of stress, in the direction normal to the surface of the specimen, with respect to strain in the normal direction, with all other strains held constant. For mapping elastic constant variations a function generator 28 is used for which $$f_{operating} = \frac{nc}{2d}(1 - \frac{\Delta c_{33}}{c_{33}}),$$

where $c_{33}$ is the elastic constant mapped. For mapping speed of sound variations, a function generator 28 is used for which $$f_{operating} = \frac{n}{2d}(c - \Delta c),$$

where c is the expected nominal value and $\Delta c$ is the expected variation of the speed of sound in specimen S. For either situation, both sides of the resonance curve used would not be traversed, for reasons given above. The function generators used would then have inputs of n, c, d, $\Delta c_{33}$ and $c_{33}$ for mapping elastic constant, or of n, d, c and $\Delta c$ for mapping speed of sound.

Since a shift in the spectral position of a resonance peak is caused by change in specimen S thickness, elastic constant, or speed of sound, it follows that certain of these three factors should be held constant while changes in the other factor are being monitored and mapped. Thus, this apparatus can be used to measure specimen S thickness for a specimen having a uniform elastic constant throughout, and can be used to map changes in specimen elastic constant for a specimen having uniform thickness. Similarly, thickness should be uniform for a specimen mapped for speed of sound variations. Darkness and lightness of the map for a elastic constant or speed of sound map would vary in a manner similar to that discussed above for maps of thickness.

The measurement sensitivity of this apparatus can be increased by using higher order frequency resonances.

Further information on resonance peak position variation with certain material properties is given in Scott, W. R. *Ultrasonic Spectrum Analysis for NDT of Layered Composite Materials.* Report No. NADC-75324-30. (NTIS Accession No. AD-A028 856/3GA, abstracted Oct. 29, 1976).

In summary, operation of the foregoing invention is as follows. Scanner 17 powered by motor means 18 moves transducer 16 across specimen S. Simultaneously, transmitter 20 controlled by clock 21 produces pulses A which are converted by transducer 16 into pulses of ultrasound. These pulses of ultrasound are used to interrogate specimen S, whose reverberation response is received by transducer 16. Transducer 16 converts the received response into an electrical signal B which is amplified by amplifier 23 and time-gated by gate 24. The signal produced by gate 24 is filtered by variable filter 26 controlled by function generator 28. Variable filter 26 produces a signal of very narrow bandwidth centered about a frequency located on a resonance peak or valley for the specimen S. This signal is demodulated by rectifier 30 and low pass filter 32 to produce a direct-current signal $D_i$ of slowly varying amplitude whose amplitude indicates the value of the varying material property of specimen S which is being mapped. Signal $D_i$ is provided to pen 34 of recorder 35 to control the gray level or intensity of the pen. Pen 34 is controlled by motor means 18 to move synchronously with transducer 16, producing a map of variations of a material property, such as thickness, of specimen S with location on the specimen.

It should be understood that the present invention can be used in similar fashion with similar operation with other interrogation radiation than ultrasound. Acoustic energy can be used for thick specimens. X-rays can be used to obtain Bragg reflections to show inter-atomic spacing in the specimen S, which varies with residual stress. The Mossbauer effect can be used to interrogate the velocity distributions of atoms and the distribution of the local electromagnetic field of the surrounding atoms. Also, gate 24 need not trigger on the first response echo, but can be set entirely by clock 21 according to samplings made on specimen S before actually beginning the scan. In addition, besides a pen recorder, an intensity modulated storage oscilloscope, or other recorder, can be used as recorder 35, with the X and Y coordinates being based upon the coordinates of the transducer, and signal $D_i$ being used for intensity modulation. Also, any appropriate energy-producing and energy receiving means can be substituted for transducer 16.

Thus there has been provided novel material scanning apparatus producing a pictorial display of variations of certain material properties in a material specimen. This apparatus can be used with both monolithic and laminated specimens. Such measurements are important in general inspection for quality control of materials. Where specimen thickness is mapped, precise predictions of the position of material breaks or failures can be made, since these would be most likely to appear in thin areas, the position of which the invention can show with great precision. Failures can thus be anticipated, or avoided by appropriate measures.

Obviously, many modifications and variations of the present invention are possible in light of the above teachings. It is therefore to be understood that within the scope of the appended claims the invention may be practiced otherwise than as specifically described.

What is claimed is:

1. Apparatus for measuring a property in a specimen of material, comprising:
    transmitting means for transmitting a pulse of energy to the specimen at a selected location;
    gating means receiving a response signal produced by said energy pulse in the specimen for selecting and passing a predetermined time-portion of the response signal as a gated electrical signal;
    function generator means responsive to signals indicative of speed of sound in the specimen, order of the resonance extrema, nominal thickness of the specimen, and expected variation in specimen thickness for producing an output signal indicative of a frequency near one of the resonance extrema of the specimen;
    filter means receiving the gated signal and the output signal for producing a filtered signal of narrow bandwidth centered about said frequency and comprising a variable frequency bandpass filter; and
    indicating means receiving the filtered signal for indicating the amplitude of the filtered signal.

2. Apparatus as recited in claim 1 further comprising:
    motor means connected to said transmitting means and to said indicating means for synchronously and simultaneously positioning said transmitter means at the selected location and positioning said indicator means at a corresponding location.

3. Apparatus as recited in claim 2 wherein said indicating means comprises:
    a rectifier receiving the filtered signal for producing a rectified signal;
    a low pass filter receiving the rectified signal for producing a varying signal; and
    recording means receiving the varying signal and operatively connected to said motor means for recording the amplitude of the varying signal with respect to position of said transmitting means.

4. Apparatus as recited in claim 1 wherein:
    the specimen is of uniform elasticity throughout; and
    said function generator means produces a signal indicative of a function of the speed of sound in the specimen, the desired sensitivity and the nominal thickness and expected variation of thickness of the specimen;
    whereby the resulting measurement is the thickness of the specimen.

5. Apparatus as recited in claim 1 wherein the energy is ultrasound; and said function generator means comprises setting means for setting said frequency at $$cn/2d \pm cn\Delta d/2d^2$$

where c is the speed of sound in the specimen, n is an integer, d is the nominal thickness of the specimen, and $\Delta d$ is the expected variation in specimen thickness.

6. Apparatus as recited in claim 1, further comprising:
    receiving means receiving the response signal for providing the response signal to said gating means.

7. Apparatus as recited in claim 1, further comprising:
    reflector means disposed adjacent the side of the specimen distant from said transmitting means for reflecting the response signal to the specimen.

8. Apparatus as recited in claim 1 wherein said transmitting means comprises a broad-band transducer.

9. A method for measuring a property in a specimen of material, comprising:
    transmitting a broad-band narrow pulse of energy to the specimen at a selected location;
    gating a predetermined time-portion of a response signal produced by said energy pulse in the specimen to produce a gated signal;
    producing, responsive to signals provided in a function generator which are indicative of speed of sound in the specimen, order of the resonance extrema, nominal thickness of the specimen, and expected variation in the measured property, an output signal indicative of a frequency near one of the resonance extrema of the specimen;
    filtering the gated signal to produce a filtered signal of narrow bandwidth centered about the frequency indicated by the output signal; and
    indicating on a display the amplitude of the filtered signal.

10. A method as recited in claim 9 wherein the energy is ultrasound; and the indicating step comprises recording on a display the amplitude of the filtered signal on a position representative of the selected location.

* * * * *